United States Patent
Goswami et al.

(10) Patent No.: US 12,055,737 B2
(45) Date of Patent: Aug. 6, 2024

(54) ALIGNED AND STACKED HIGH-ASPECT RATIO METALLIZED STRUCTURES

(71) Applicant: GE Precision Healthcare LLC, Wauwatosa, WI (US)

(72) Inventors: Shubhodeep Goswami, Schenectady, NY (US); Bruno Kristiaan Bernard De Man, Clifton Park, NY (US); Uwe Wiedmann, Clifton Park, NY (US); Charles Alexander Szymanski, Ballston Spa, NY (US)

(73) Assignee: GE PRECISION HEALTHCARE LLC, Wauwatosa, WI (US)

(*) Notice: Subject to any disclaimer, the term of this patent is extended or adjusted under 35 U.S.C. 154(b) by 259 days.

(21) Appl. No.: 17/747,356

(22) Filed: May 18, 2022

(65) Prior Publication Data
US 2023/0375759 A1 Nov. 23, 2023

(51) Int. Cl.
*G02B 5/18* (2006.01)
*A61B 6/03* (2006.01)

(52) U.S. Cl.
CPC ............ *G02B 5/1838* (2013.01); *A61B 6/032* (2013.01); *G02B 5/1852* (2013.01)

(58) Field of Classification Search
None
See application file for complete search history.

(56) References Cited

U.S. PATENT DOCUMENTS

| 7,164,138 B2 * | 1/2007 | McGregor | G01T 3/00 250/390.01 |
| 7,435,965 B2 * | 10/2008 | Fuchs | G01T 1/202 250/370.11 |
| 7,639,786 B2 * | 12/2009 | Baumann | A61B 6/4291 378/5 |

(Continued)

FOREIGN PATENT DOCUMENTS

| CN | 108859098 A | 11/2018 |
| CN | 108885917 A | 11/2018 |
| EP | 2681745 A1 | 1/2014 |

OTHER PUBLICATIONS

Fuller, Sawyer B., et al.; "Ink-jet Printed Nanoparticle Microelectromechanical Systems", Journal of Microelectromechanical Systems, vol. 11, Issue: 1, pp. 54-60, Feb. 2002.

(Continued)

*Primary Examiner* — David P Porta
*Assistant Examiner* — Djura Malevic
(74) *Attorney, Agent, or Firm* — Fletcher Yoder P.C.

(57) ABSTRACT

A method for forming a multi-layered, stacked grid structure includes aligning a first grid structure with a second grid structure, wherein both the first grid structure and the second grid structure each include a substrate in which a plurality of trenches are formed and a cured carrier fluid disposed within the plurality of trenches, and wherein a plurality of nanoparticles are suspended within the cured carrier fluid. The method also includes, upon aligning the first grid structure and the second grid structure so that their respective plural- (Continued)

ity of trenches are aligned in the same orientation, joining the first grid structure and the second grid structure together to form the multi-layered, stacked grid structure.

20 Claims, 15 Drawing Sheets

(56) References Cited

U.S. PATENT DOCUMENTS

| | | | | |
|---|---|---|---|---|
| 7,652,261 | B1* | 1/2010 | Wilson | G01T 1/16 250/370.11 |
| 7,855,372 | B2* | 12/2010 | McGregor | G01T 3/08 250/370.05 |
| 8,017,860 | B2* | 9/2011 | Lee | H01L 31/074 136/265 |
| 8,129,688 | B2* | 3/2012 | Karim | G01T 1/241 250/370.01 |
| 8,243,879 | B2 | 8/2012 | Itoh et al. | |
| 8,454,859 | B2 | 6/2013 | Lowenthal et al. | |
| 8,718,228 | B2* | 5/2014 | Nakamura | A61B 6/484 378/36 |
| 8,778,715 | B2* | 7/2014 | Bellinger | H01L 31/18 438/700 |
| 8,895,934 | B2* | 11/2014 | Wang | B81C 1/00619 250/363.06 |
| 8,969,900 | B2* | 3/2015 | Sabathil | H01L 33/20 257/E33.068 |
| 9,036,773 | B2* | 5/2015 | David | G01N 23/041 378/36 |
| 9,105,776 | B2* | 8/2015 | Lee | H01L 31/0352 |
| 9,230,703 | B2* | 1/2016 | Mohr | G21K 1/06 |
| 9,422,159 | B2* | 8/2016 | Colby | B82Y 20/00 |
| 9,425,234 | B2* | 8/2016 | Colby | G01T 1/208 |
| 9,597,050 | B2* | 3/2017 | Roessl | A61B 6/502 |
| 9,700,267 | B2* | 7/2017 | Baturin | A61B 6/4291 |
| 9,720,330 | B2* | 8/2017 | Guo | H10K 71/621 |
| 9,861,330 | B2* | 1/2018 | Rössl | A61B 6/4291 |
| 9,891,327 | B2* | 2/2018 | Teshima | C23C 28/32 |
| 9,966,503 | B2* | 5/2018 | Straßburg | H01L 33/56 |
| 10,058,300 | B2* | 8/2018 | Baturin | A61B 6/4035 |
| 10,079,318 | B2 | 9/2018 | Hilali et al. | |
| 10,096,098 | B2* | 10/2018 | Baturin | G06T 5/50 |
| 10,121,818 | B2* | 11/2018 | Colby | B82Y 15/00 |
| 10,304,580 | B2* | 5/2019 | Yun | G21K 7/00 |
| 10,451,751 | B2* | 10/2019 | Cao | G01T 3/08 |
| 10,559,393 | B2* | 2/2020 | Proksa | A61B 6/484 |
| 10,578,563 | B2* | 3/2020 | Baturin | G01N 23/04 |
| 10,593,722 | B2* | 3/2020 | Colby | B82Y 15/00 |
| 10,656,105 | B2* | 5/2020 | Yun | A61B 6/4035 |
| 10,658,145 | B2* | 5/2020 | Yun | H01J 35/12 |
| 10,825,856 | B2* | 11/2020 | Colby | G01T 1/208 |
| 11,000,249 | B2* | 5/2021 | Daerr | A61B 6/484 |
| RE48,612 | E* | 6/2021 | Yun | A61B 6/4291 |
| 11,156,727 | B2* | 10/2021 | Shedlock | G01T 1/20186 |
| 11,163,230 | B2* | 11/2021 | Verschuuren | C08L 83/04 |
| 11,175,243 | B1* | 11/2021 | Yun | G01N 23/04 |
| 11,387,438 | B2* | 7/2022 | Watkins | H01M 4/131 |
| 11,522,099 | B2* | 12/2022 | Cao | H01L 27/14696 |
| 11,545,516 | B2* | 1/2023 | Colby | H01L 27/14629 |
| 11,759,159 | B2* | 9/2023 | Koehler | A61B 6/484 378/62 |
| 11,764,057 | B2* | 9/2023 | Liu | H01L 21/02428 257/49 |
| 11,843,015 | B2* | 12/2023 | Jang | H01L 27/14685 |
| 11,860,535 | B2* | 1/2024 | Verschuuren | B29C 33/424 |
| 11,869,918 | B2* | 1/2024 | Colby | H01L 27/14663 |
| 11,885,755 | B2* | 1/2024 | Yun | G01N 23/2076 |
| 2004/0026121 | A1* | 2/2004 | Bernds | H01L 21/31133 430/311 |
| 2004/0054980 | A1* | 3/2004 | Perlov | H05K 3/20 438/703 |
| 2005/0118338 | A1* | 6/2005 | Stebe | B82Y 30/00 427/372.2 |
| 2005/0207012 | A1* | 9/2005 | Arnold | G03F 7/70316 359/558 |
| 2007/0183579 | A1* | 8/2007 | Baumann | A61B 6/4291 430/5 |
| 2007/0190298 | A1 | 8/2007 | Hampden-Smith et al. | |
| 2007/0264488 | A1* | 11/2007 | Lee | H01L 31/074 428/323 |
| 2008/0011934 | A1* | 1/2008 | Verschuuren | B29C 33/60 264/225 |
| 2008/0092953 | A1* | 4/2008 | Lee | B82Y 10/00 136/252 |
| 2009/0159121 | A1 | 6/2009 | Yang et al. | |
| 2009/0211626 | A1* | 8/2009 | Akimoto | H01L 31/022425 252/514 |
| 2010/0038649 | A1* | 2/2010 | Lee | B29C 33/56 427/595 |
| 2010/0133418 | A1* | 6/2010 | Sargent | H01L 21/02601 977/773 |
| 2010/0227433 | A1* | 9/2010 | Konno | H01B 1/22 257/E21.159 |
| 2011/0192457 | A1* | 8/2011 | Nakayama | H01L 31/02168 257/E31.127 |
| 2012/0070911 | A1* | 3/2012 | Peyrade | B01L 3/502761 422/69 |
| 2013/0098431 | A1* | 4/2013 | Chen | H01B 1/22 977/773 |
| 2013/0344636 | A1* | 12/2013 | Bellinger | G01T 3/00 977/773 |
| 2014/0124713 | A1 | 5/2014 | Majumdar et al. | |
| 2014/0264256 | A1* | 9/2014 | Nikolic | G21H 1/00 438/20 |
| 2014/0374669 | A1* | 12/2014 | Hardin | H01L 31/022425 252/513 |
| 2015/0083213 | A1* | 3/2015 | Hardin | H01L 31/022425 136/256 |
| 2015/0243812 | A1* | 8/2015 | Hardin | H01L 31/022425 252/514 |
| 2015/0293442 | A1* | 10/2015 | Kreindl | G03F 7/0015 101/32 |
| 2016/0225926 | A1* | 8/2016 | Schäfer | H01B 1/22 |
| 2016/0307942 | A1* | 10/2016 | Cheng | H01L 27/14623 |
| 2016/0356901 | A1* | 12/2016 | Shao | G01T 3/08 |
| 2016/0363673 | A1* | 12/2016 | Ahn | G01T 1/2018 |
| 2018/0073065 | A1* | 3/2018 | Bowen | B01J 19/0093 |
| 2018/0119139 | A1* | 5/2018 | Bowen | B82Y 15/00 |
| 2019/0212697 | A1* | 7/2019 | Stensborg | C09D 11/322 |
| 2019/0243237 | A1* | 8/2019 | Watkins | C09D 11/52 |
| 2019/0304877 | A1 | 10/2019 | Mobley et al. | |
| 2019/0355726 | A1* | 11/2019 | Pillarisetty | H10N 70/8833 |
| 2019/0386251 | A1* | 12/2019 | Erickson | H10K 50/858 |
| 2019/0393267 | A1* | 12/2019 | Pillarisetty | H10N 50/01 |
| 2020/0357997 | A1* | 11/2020 | Moddel | H02N 11/002 |
| 2020/0365656 | A1* | 11/2020 | Pillarisetty | H01L 29/152 |
| 2022/0375748 | A1* | 11/2022 | Liu | H01L 21/0243 |
| 2022/0415841 | A1* | 12/2022 | Sharma | H01L 24/32 |
| 2023/0044331 | A1* | 2/2023 | Sharma | H01L 25/167 |
| 2023/0044697 | A1* | 2/2023 | Sharma | G02B 6/132 |
| 2023/0058578 | A1* | 2/2023 | Goswami | H01L 21/3086 |
| 2023/0091603 | A1* | 3/2023 | Sato | H10N 19/00 136/201 |
| 2024/0094593 | A1* | 3/2024 | Dehkordi | G02F 1/29 |

OTHER PUBLICATIONS

Schneider, Julian, et al.; "Electrohydrodynamic NanoDrip Printing of High Aspect Ratio Metal Grid Transparent Electrodes", Advanced Functional Material, vol. 26, Issue: 6, pp. 833-840, Feb. 9, 2016.
U.S. Appl. No. 17/404,646, filed Aug. 17, 2021, Shaddock et al.

* cited by examiner

ALIGNED AND STACKED HIGH-ASPECT RATIO METALLIZED STRUCTURES

BACKGROUND

The subject matter disclosed herein relates to aligned and stacked high-aspect ratio gratings, which may be used in various mechanical systems including imaging systems.

Various mechanical and micro-mechanical systems may employ gratings or grids that include some form of trench or other opening defined at least partially by sidewalls (e.g., vertical sidewalls). Such gratings or grids may be employed to limit or collimate the passage of energy or material from one side of the grating or grid to the opposite side or may perform other functions where the trench or other sidewall structures facilitate the functioning of the overall system.

In practice, a trench of such a structure may be characterized by an aspect ratio, which is the ratio of one dimension of the trench relative to another dimension of the trench. For example, an aspect ratio of such a trench may generally be equated to the ratio of the longer dimension (e.g., height) to the shorter dimension (e.g., width) of the trench. Thus, the taller and narrower the trench, the higher the aspect ratio of the trench.

In general, it may be difficult to pattern vertical sidewalls of such a trench beyond aspect ratios of 20 when combined with trench widths larger than 0.5 microns up to 50 microns in silicon using conventional photoresists. Metal masking may be employed but has been an imperfect solution due to re-sputtering and re-deposition of the metal into the etched regions and defects due to undesired micro-masking in the trench regions. In addition, in some contexts it may be useful to fill the trenches with a separate material (e.g., a metal). However, traditional methods to fill metal into deep or high-aspect ratio trenches typically involves expensive cleanroom based processing (e.g., electron-beam evaporation, electroplating, sputtering, and so forth).

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the disclosed subject matter may encompass a variety of forms that may be similar to or different from the embodiments set forth below.

In one embodiment, a method for forming a multi-layered, stacked grid structure is provided. The method includes aligning a first grid structure with a second grid structure, wherein both the first grid structure and the second grid structure each include a substrate in which a plurality of trenches are formed and a cured carrier fluid disposed within the plurality of trenches, and wherein a plurality of nano-particles are suspended within the cured carrier fluid. The method also includes, upon aligning the first grid structure and the second grid structure so that their respective plurality of trenches are aligned in the same orientation, joining the first grid structure and the second grid structure together to form the multi-layered, stacked grid structure.

In an additional embodiment, a method for forming a stacked metallized grid structure is provided. The method includes optically aligning a plurality of metallized grid structures on a substrate utilizing an optical camera of a wafer bonding system and fiducial marks on the substrate. Each metallized grid structure of the plurality of metallized grid structures includes a respective substrate in which a plurality of trenches are formed and a cured carrier fluid disposed within the plurality of trenches, wherein a plurality of nano-particles having a high Z material are suspended within the cured carrier fluid. The method also includes, upon optically aligning the plurality of metallized grid structures so that their respective plurality of trenches are aligned in the same orientation, joining the plurality of metallized grid structures together to form the stacked metallized grid structure.

In a further embodiment, an imaging grating is provided. The imaging grating includes a plurality of metallized grid structures bonded together in a stacked arrangement. Each metallized grid structure of the plurality of metallized grid structures includes a respective substrate in which a plurality of trenches are formed and a cured carrier fluid disposed within the plurality of trenches, wherein a plurality of nano-particles having a high Z material are suspended within the cured carrier fluid, and wherein the respective plurality of trenches of the plurality of metallized grid structures are aligned in the same orientation. Each metallized grid structure was individually fabricated prior to bonding of the plurality of metallized grid structures together.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
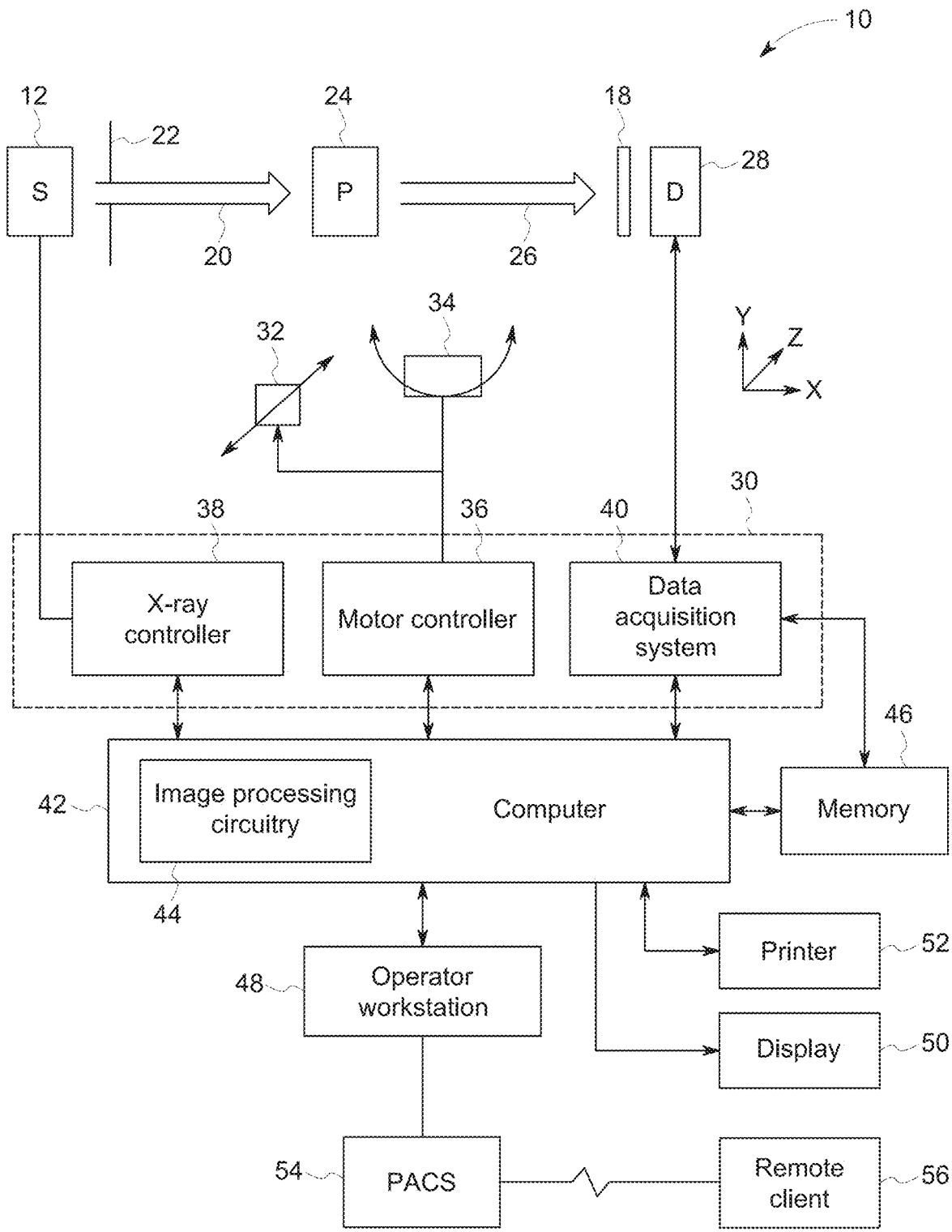
FIG. 1 depicts components of a computed tomography imaging system, in accordance with certain aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging (e.g., X-ray imaging gratings), it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts in which high-aspect ratio sidewall structures (e.g., grids, trenched and/or segmented gratings, Micro-Electro-Mechanical Systems (MEMS) devices, and so forth) are employed. For example, the present techniques may be employed in the manufacture of capacitive MEMS devices, electrostatic MEMS devices, inertial MEMS devices, magnetic MEMS devices, electromagnetic MEMS devices, radiofrequency MEMS devices, and other MEMS structures, as well as Through Silicon Vias (TSVs), fin field-effect transistors (FinFETs), interconnect structures in system-on-a-chip (SOC) or complementary metal-oxide semiconductor (CMOS) devices, and so forth.

In general, it is difficult to pattern vertical sidewalls (such as may be present in formed trenches) having aspect ratios greater than 20 in combination with trench widths larger than 0.5 microns up to 50 microns in a substrate (such as a silicon substrate) using conventional photoresists. Approaches employing metal masking, for example, may result in re-sputtering and re-deposition of the metal into the etched regions and/or defects from undesired micro-masking in the trench regions.

The present techniques relate to various aspects of forming and filling high-aspect ratio trench structures (e.g., trench structures having an aspect ratio of 20 or greater, including aspect ratios in the range of 20:1 up to and including 50:1 or greater). By way of example, in one implementation a method to fabricate high-aspect ratio trenches in a substrate (such as a silicon substrate or wafer) is provided using a patterned photoresist on a mask layer (e.g., an evaporated aluminum mask layer), which acts as deep reactive ion etch mask during a Bosch process. In accordance with this approach, a high-aspect ratio trench can be formed having vertical side walls, very low re-sputtering of the mask material (e.g., aluminum metal), and with negligible micro-masking of the open trench regions.

In some instances it may be desirable to fill such high-aspect ratio trench structures with a metal or other substrate to provide certain functionality associated with the fill material. Traditional methods to fill metal into deep trench structures typically involve expensive cleanroom based processing (e.g., e-beam evaporation, electroplating, sputtering, atomic layer deposition, etc.).

With this in mind, a further aspect of the present techniques include filling metal into such high-aspect ratio trench structures using non-cleanroom additive approaches (e.g., squeegee, screen printing, or roll printing approaches). By way of example, the present techniques include approaches for filling high-aspect ratio trench structures with high atomic weight (i.e., high-Z) elements (e.g., materials having atomic numbers (i.e., Z values) of 72 and beyond, such as, but not limited to hafnium, tantalum, tungsten, rhenium, osmium, iridium, platinum, gold, mercury, thallium, lead, bismuth, polonium, depleted uranium, and so forth), though other elements, such as palladium, may also be employed in other embodiments. These techniques may allow for the formation of periodic metal gratings using novel and inexpensive nano-particle formulations through screen printing and roll printing. Such periodic high-aspect ratio metallized gratings are used in applications ranging from X-ray imaging for healthcare, X-ray inspection systems for materials analysis, X-ray lithography for nanofabrication of capacitive MEMs, micro-inductors, and so forth.

In one implementation nano-particles of high atomic weight elements (e.g., metal nano-particles) are dispersed in solvent matrices and screen printed and/or roll printed into pre-fabricated high-aspect ratio trenches with periods at the sub-20 μm scale. Screen printing and/or roll printing of these nano-particulate inks (or other nano-particle containing media) is readily scalable to any substrate size (e.g., wafers, panels, flexible rolls, and so forth) and to high volume production. Correspondingly, advantages of this technique relative to prior techniques include, but are not limited to, reduced processing step requirements, reduced equipment costs, higher throughput per unit area of substrate, flexible fabrication across whole range of nano-particle compositions, easier scalability across a range of aspect ratios and substrate sizes, and so forth.

In one implementation, after fabrication of individual layers or grid structures (e.g., metallized gratings) utilizing the disclosed techniques, multiple layers may be aligned and bonded together to form a multi-layer stacked and bonded metallized structure or grating. For example, fiducial marks on a substrate (e.g., wafer) may be utilized for optical alignment of the individual layers (e.g., utilizing an optical camera of a wafer bonding system). Aligning and stacking multiple layers in the stacked metallized structure effectively increases the effective aspect ratio relative to a single layer by a multiple of the number of layers in the stacked metallized structure. For example, stacked metallized structures having 2, 3, 4, or more layers would have an effective aspect ratio of 2×, 3×, 4×, or more the aspect ratio of a single layer. In addition, the stacked metallized structure is scalable with no upper limit on height. Further, the amount of metal per layer may be increased due to the multiple layers within the stacked metallized structure, thus, improving the ability to block/attenuate X-ray incident energies relative to a single layer. As a result, the signal-to-noise ratio as resolved by an imaging detector in an overall X-ray imaging system is improved.

With the preceding discussion in mind, FIG. 1 illustrates an embodiment of an imaging system 10 for acquiring and processing image data in accordance with structures and approaches discussed herein. That is, the depicted type of imaging system 10 is an example of one type of imaging system that may benefit from or otherwise utilize components made in accordance with the techniques described herein (e.g., high-aspect ratio metallized gratings or grids having multiple layers in an aligned and stacked arrangement). Though, as noted herein, other types of systems (e.g., non-imaging systems, non-medical systems, and so forth) may also utilize components made in accordance with the techniques described herein.

In the illustrated example, system 10 is a computed tomography (CT) system designed to acquire X-ray projection data and to reconstruct the projection data into volumetric reconstructions for display and analysis. The CT imaging system 10 includes one or more X-ray sources 12, such as one or more X-ray tubes or solid state emission structures which allow X-ray generation at one or more energy spectra during an imaging session.

In certain implementations, the source 12 may be positioned proximate to a pre-patient collimator and/or filter assembly 22 that may be used to steer the X-ray beam 20, to define the shape (such as by limiting off-angle emissions) and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry, between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-ray photons 20, resulting in attenuated X-ray photons 26 that impinge upon a pixelated detector array 28 formed by a plurality of detector elements (e.g., pixels) arranged in an array. In the depicted example, the attenuated X-ray photons 26 pass through a collimator 18 (e.g., an anti-scatter grid) prior to reaching the detector array 28. As discussed herein, the collimator 18 may consist of a plurality of blades or other elements aligned substantially perpendicular to the surface of the detector array 28 and formed from an attenuating material that limit or prevent X-ray photons 26 traveling at off-angles (e.g., scattered X-rays) from reaching the detector array 28. The electrical signals reaching the detector array 28 are detected and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols, and may process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move the subject 24 and/or components of the imaging system 10, respectively. For example, in a CT system, the radiation source 12 and detector 28 rotate about the object (e.g., patient 24) to acquire X-ray transmission data over a range of angular views. Thus, in a real-world implementation, the imaging system 10 is configured to generate X-ray transmission data corresponding to each of the plurality of angular positions (e.g., 360°, 180°+a fan beam angle (a), and so forth) covering an entire scanning area of interest.

The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal spot size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the detector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation. By way of example, the image processing circuitry 44 of the computer 42 may be configured to generate a diagnostic image.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data or images, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

Figure 2:
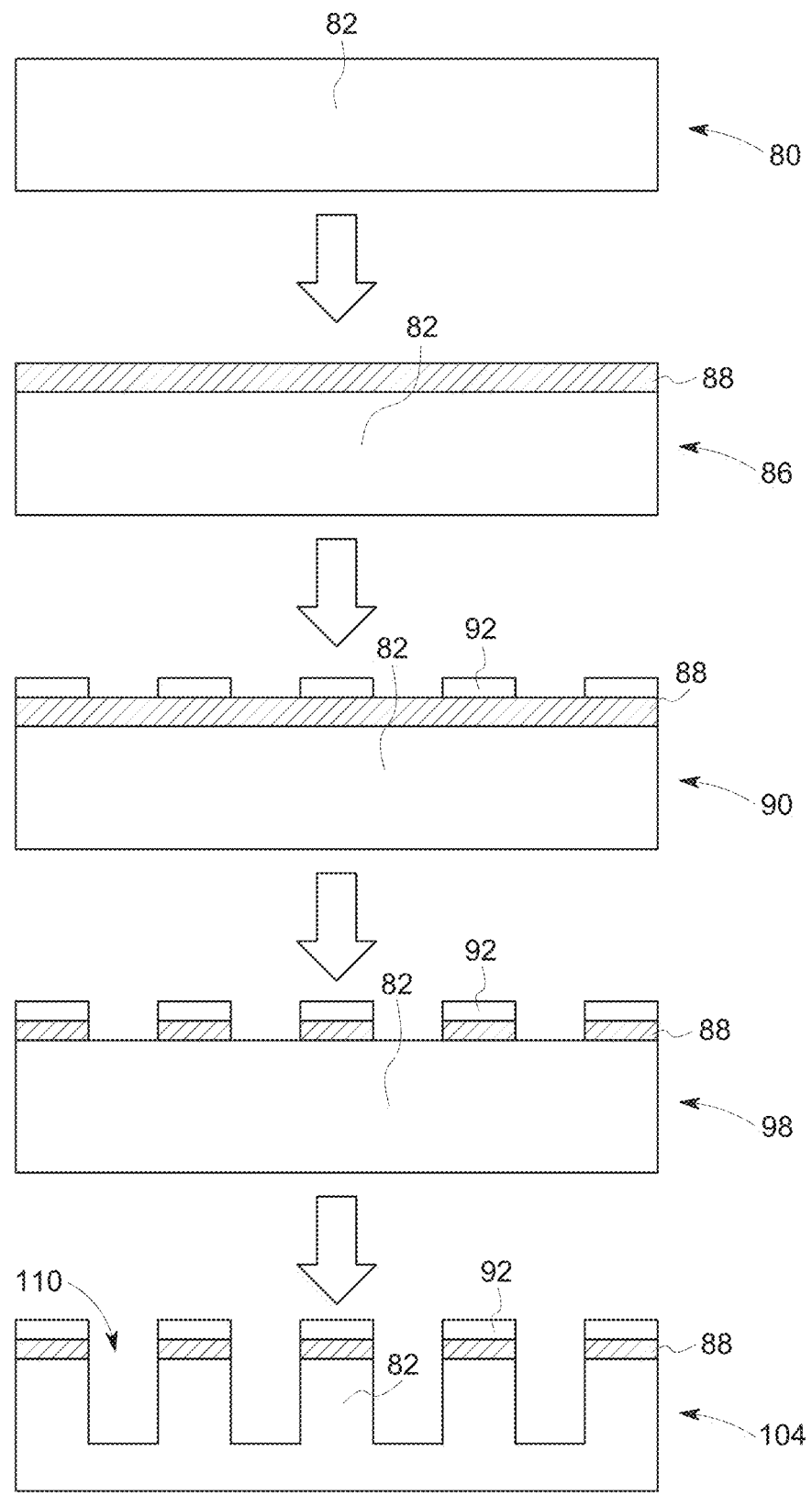
FIG. 2 depicts a flow diagram of steps of a process for forming high-aspect ratio trenches within a substrate, in accordance with certain aspects of the present disclosure.

As noted above, certain features of the imaging system 10 (or other suitable system) may utilize components that include high aspect ratio trenches (metallized or otherwise) as part of their structure. For example, in the context of an imaging system, absorption gratings, phase gratings, anti-scatter features, collimation features, and so forth may include such trench structures and may benefit from higher aspect ratio trenches than what is conventionally possible. With the preceding discussion of an overall imaging system 10 in mind, and turning to FIG. 2, an example of an approach for forming high-aspect ratio trench structures is illustrated as a process flow.

In this example, a substrate (e.g., a silicon wafer, such as a standard (1, 0, 0) silicon wafer) undergoes a high-aspect ratio patterning process using a patterned resist and mask (e.g., a metal or other hard mask, such as an aluminum mask). For the purpose of illustration and explanation, the following example and other examples herein may be provided in the context of a silicon substrate or wafer and an aluminum mask so as to provide a real-world context. However it should be appreciated that such examples are for the purpose of illustration only, and that in practice any suitable substrate and/or mask may be employed. With this in mind, in one implementation, a deep reactive ion etch is performed on the silicon wafer. In step 80 of FIG. 2, a silicon wafer 82 is initially provided as part of the process. As step 86 aluminum is evaporated and then deposited onto the silicon wafer 82 as an aluminum layer 88, such as using electron beam (e-beam) evaporation. In one implementation, the aluminum layer 88 has a thickness of approximately 0.5 μm or greater. More generally, the thickness of the aluminum mask layer and photoresist may be determined based on the ratio of vertical etch rates of silicon being greater than that of aluminum and photoresist.

At step 90 a photoresist layer 92 is coated over the aluminum layer 88 and patterned (e.g., photolithographically patterned) to correspond to the trench structures to be formed, thereby forming the desired device layer. By way of example, this step may include some or all of the sub-steps of: spin-coating the photoresist layer 92 onto the aluminum layer 88, baking or otherwise setting the photoresist material on the substrate and removing any remaining solvent, exposing the photoresist material to some form of radiation to produce the desired pattern image on the layer of photoresist, and developing the photoresist pattern on the aluminum layer 88 based on the pattern image so as to form the physical pattern on the aluminum layer 88. In one such example of an implementation, the photoresist applied has a thickness of 7.5 μm or greater and is patterned to correspond to the trench structures to be formed.

At step 98 the aluminum layer 88 is wet etched through the pattern created by the photoresist layer 92. In this manner, the pattern of the photoresist layer 92 is applied to the aluminum layer 88 exposing the silicon 82 based upon the pattern. Lastly, at step 104, the silicon wafer stack 82 is processed in accordance with the pattern to form trenches 110. In one embodiment the silicon 82 is processed using deep reactive ion etch (DRIE) equipment, such as using a SF6/C4F8/O2 plasma (e.g., in accordance with a Bosch process), to form trenches 110 having a high-aspect ratio (e.g., an aspect ratio greater than or equal to 20:1, including greater than or equal to 25:1 30:1, 35:1, 40:1, 45:1, and so forth up to and including 50:1) and substantially vertical sidewall angles. In one such example, SF6/C4F8 plasma may be suitable for performing the etch step because aluminum 88 and photoresist 92 have a lower vertical etch rate relative to silicon 82 using SF6/C4F8 plasma, leaving the aluminum patterned layer 88 largely intact while the silicon 82 is etched. In addition, the photoresist layer 92 in this example protects the aluminum layer 88 from being exposed to the plasma on the upper surface, and thereby prevents re-sputtering and micro-masking of the trench bottoms and sidewalls during the initial phase of the etch.

Figure 3:
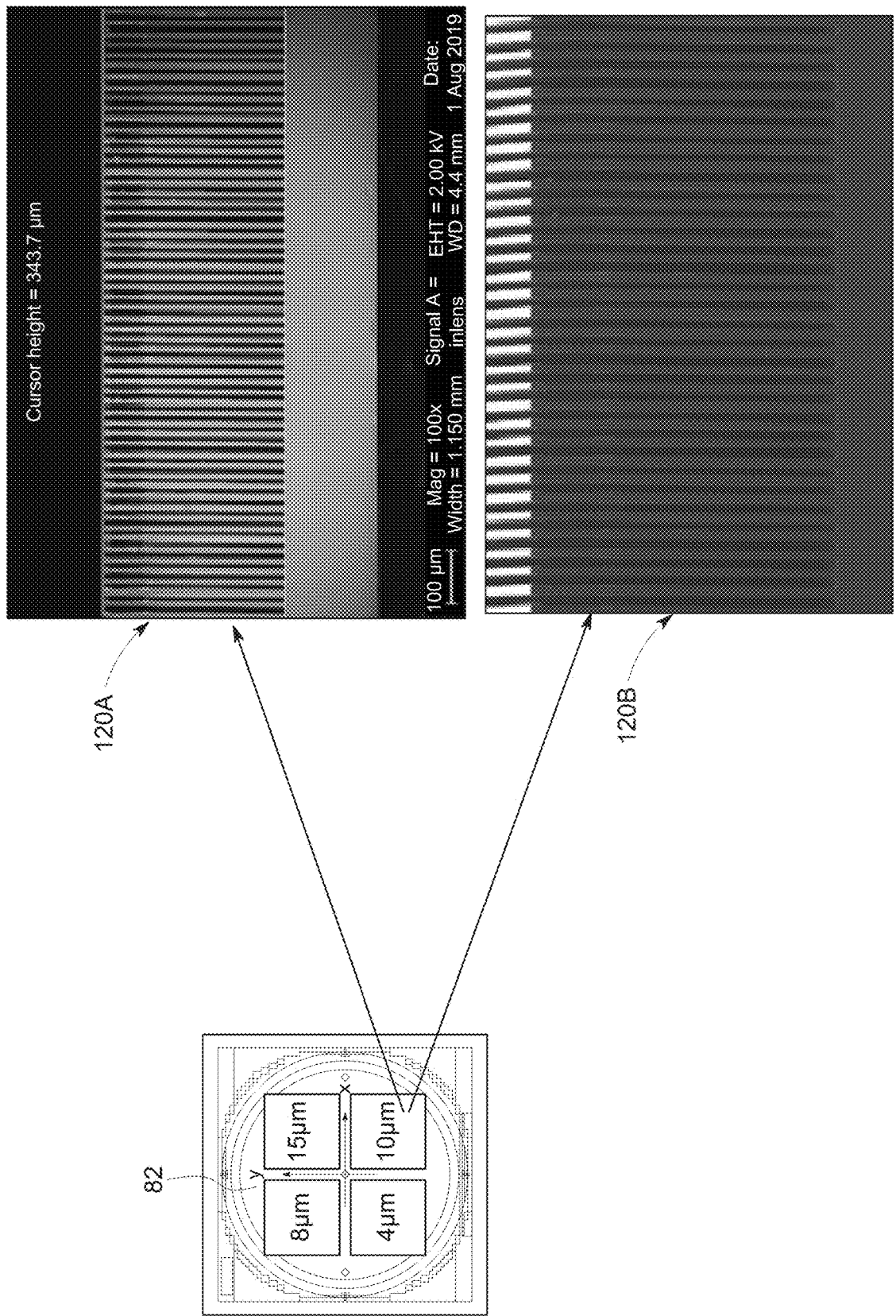
FIG. 3 illustrates using a schematic and images, examples of high-aspect ratio trenches formed in accordance with certain aspects of the present disclosure.

With the preceding in mind, the present techniques were tested in attempts to pattern sub-10 μm trenches (with a duty cycle of 50%) to etch depths greater than 300 μm (e.g., greater than 342 μm). Aspects of these studies are illustrated in FIG. 3 where a representation of a silicon wafer 82, processed as described above, is schematically illustrated along with scanning electron micrograph images 120A, 120B illustrating a trench structure formed using the techniques described herein. An aluminum mask and overlying photoresist was patterned on the silicon wafer 82 with equal number of lines/space. Space critical dimensions (CDs) ranged, as shown, from 15 μm, 10 μm, 8 μm, and 4 μm. In this study, the goal was to etch trenches 110 having a depth greater than 300 μm and corresponding aspect ratios greater than 20:1 or 30:1 with an approximately 10 μm space CD or less at ~50% duty cycle. A maximum trench depth of approximately 342 μm was obtained after a DRIE etch time of approximately 180 minutes. As shown in the images 120, the maximum aspect ratio achieved was approximately 34:1 for 10 μm spacing (i.e., a 342 μm trench depth). Greater than 90% of the initial aluminum mask layer deposited remained after the approximately 180 minute DRIE etch time and, as noted above, the silicon etch depth was approximately 342 μm). The DRIE etch time was essentially limited by equipment/operator availability and total thickness of the starting silicon substrate.

Figure 4:
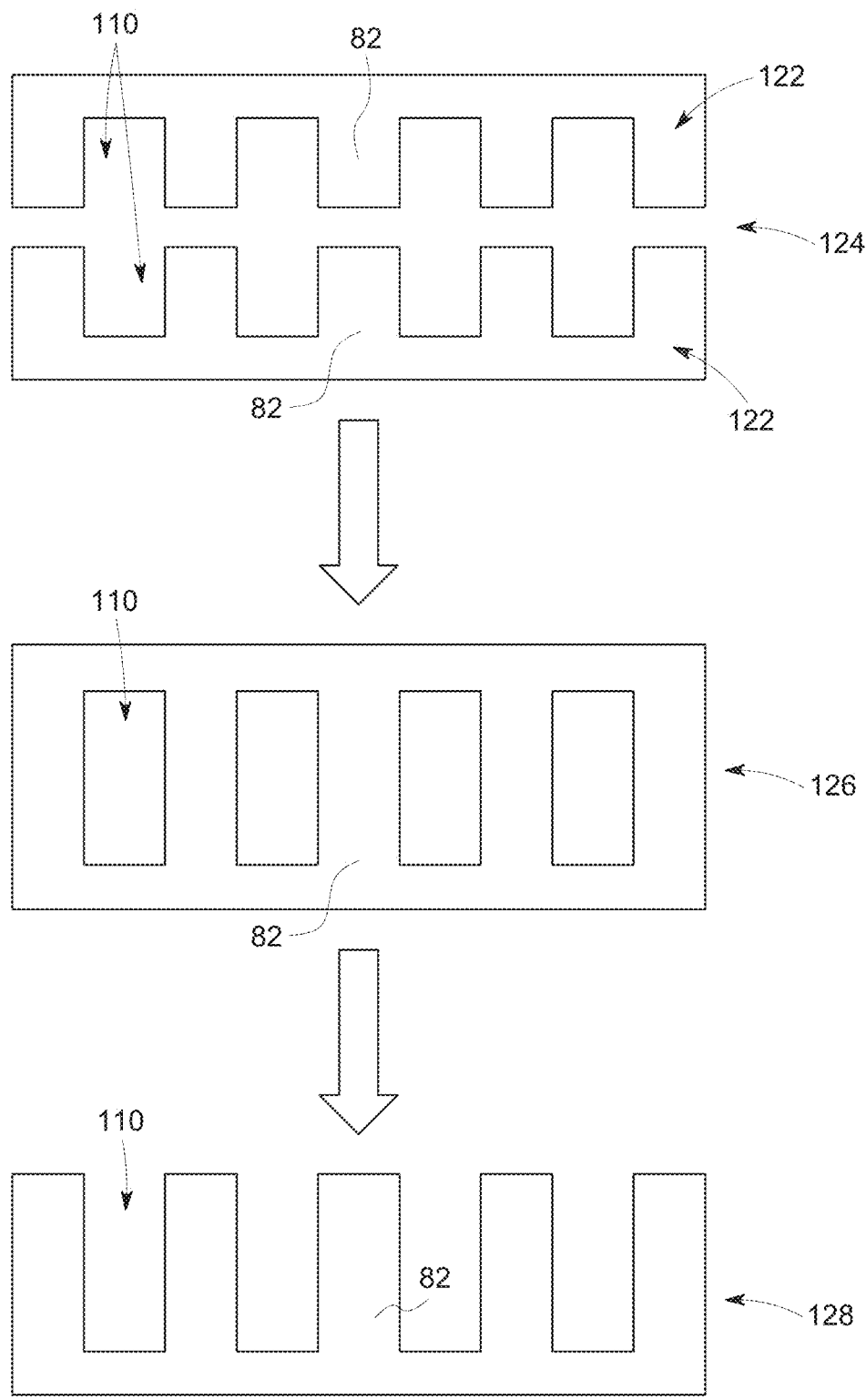
FIG. 4 depicts a process flow of steps by which structures formed with high-aspect ratio trenches may be combined to form higher-aspect ratio trenches, in accordance with certain aspects of the present disclosure.

It should also be appreciated that structures (e.g., wafers) in which trench structures 110 have been formed in accordance with this approach may be "stacked" or otherwise assembled together to form trenches having even higher aspect ratios. For example, turning to FIG. 4, two opposing trench structure containing wafers or surfaces 122 may be aligned and overlayed (step 124). The structures may then be fused or joined using conventional silicon processing techniques, as shown in step 126. In the illustrated embodiment, the wafers in which the trenches 110 are formed have been processed to remove aluminum and photoresist before joining, though in other embodiments some aspects of these layers may remain. As shown in step 128, one surface of the joined structure may be etched or otherwise removed to form a new trench structure containing higher-aspect ratio trenches than were present in the initial structures. As may be appreciated, in certain implementations, this process may be repeated using the new structures to continue to achieve even higher aspect ratio trenches, though it should be appreciated that such stacked grating structures may also be formed using other stacking arrangements to achieve a comparable increase in aspect ratio and using the same or similar fabrication methods.

Figure 5:
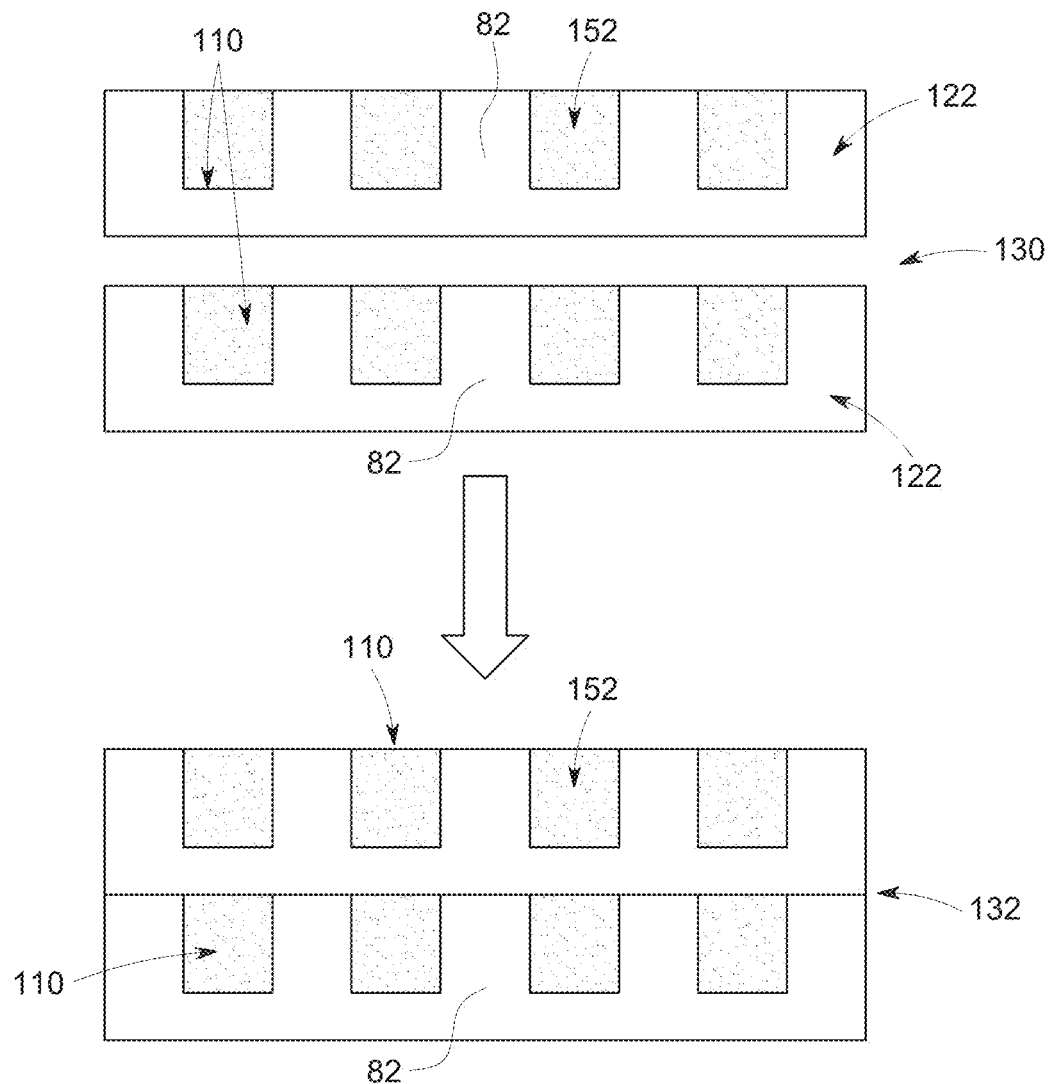
FIG. 5 depicts an additional process flow of steps by which structures formed with high-aspect ratio trenches may be combined to form an absorption grating structure having functionally higher-aspect ratio metallized trenches, in accordance with certain aspects of the present disclosure.

In a further embodiment, the structures (e.g., wafers) in which trench structures 110 have been formed and filled with high Z-metals and may be "stacked" or otherwise assembled together to form trenches that effectively or functionally have even higher aspect ratios for certain applications, such as X-ray based imaging, without removal of the silicon base layer. By way of example, and as discussed in greater detail below, the trench structures 110 may be filled with a nano-metallic powder containing composition 152 (e.g., high Z metal particulates dispersed within a resin matrix). Turning to FIG. 5, two trench structure containing wafers or surfaces 122 may be aligned and overlayed (step 130) while having the same orientation (i.e., trenches facing upward or trenches facing downward. The structures may then be fused or joined using conventional silicon processing techniques, as shown in step 132. In the illustrated embodiment, the wafers in which the trenches 110 are formed have been processed to remove aluminum and photoresist before joining, though in other embodiments some aspects of these layers may remain. In such a structure, due to the effective transparency of the silicon layer to X-rays along with the effective blocking of X-rays with the filled high Z-metal, the resulting structure effectively has higher aspect ratio metallized trenches 110 at defined periods for an imaging application, despite structurally having a break or intervening layer of silicon disposed between the trenches 110. As in the preceding example, in certain implementations this process may be repeated using the new structures to continue to achieve even higher effective aspect ratio metallized trenches.

In certain embodiments it may be further useful to fill the trench structures with a material, such as a metal or high-Z material, to fabricate a device or component. For example, such a structure with filled trenches may be useful as a grating or grid component for use in a medical imaging system (e.g., a phase or absorption grating). In practice, however, it may be difficult to fill a high-aspect ratio trench structure with a metal or metallic element or composition. For example, it may be difficult to get a homogenous or otherwise consistent fill profile of a metal or metallic composition in a high-aspect ratio structure. With this in mind, an alternative approach for filling high-aspect ratio structures is described herein.

For example, in one implementation a metallized grating may be formed by filling the high-aspect ratio trench structures with a composition of nano-particles (e.g., nano-particles of a high-Z material, such as hafnium, tantalum, rhenium, osmium, iridium, platinum, thallium, bismuth, tungsten, lead, gold, and so forth) suspended within a carrier fluid that cures to a solid state, such as an epoxy resin matrix. The process of filling the trench structures with the composition (e.g., a nano-metal ink) may be achieved using various approaches including, but not limited to: squeegeeing, roll printing, screen printing, and so forth.

Figure 6:
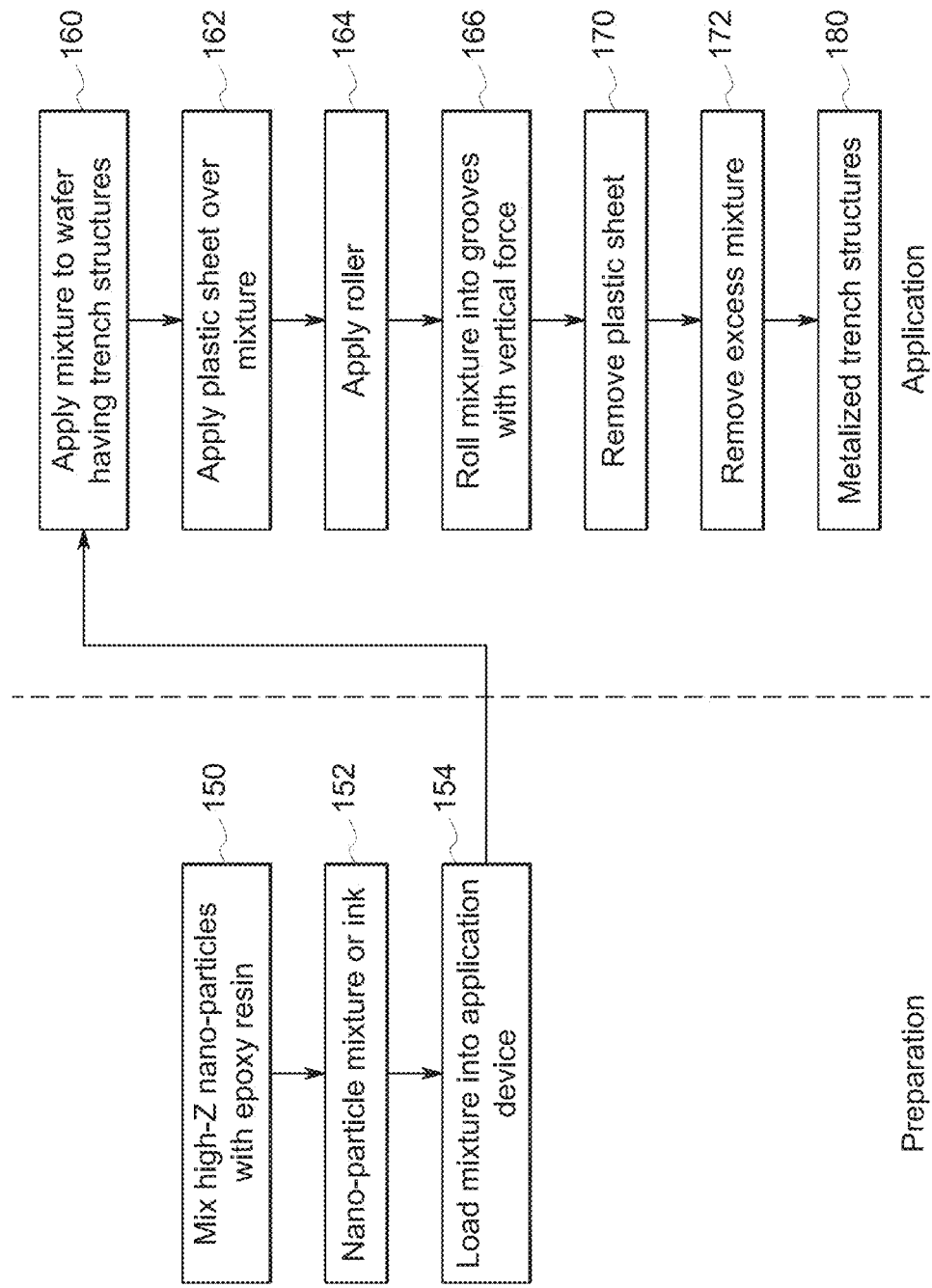
FIG. 6 depicts a flow diagram of steps of a process for filling trenches with a nano-particle mixture, in accordance with certain aspects of the present disclosure.

A process flow for one such implementation is provided in FIG. 6. In this example, preparation steps (leftmost) and application steps (rightmost) are both shown. In accordance with this example, a mixture (e.g., a nano-metal ink) is created by combining or mixing (step 150) nano-particles of a high-Z material (e.g., tungsten, lead, gold, and so forth) with a suitable non-solid medium or carrier fluid that can be set or cured to solidity, such as an epoxy resin matrix employing a curing agent or condition. As shown in FIG. 6, the resulting mixture 152 is loaded (step 154) into a suitable application device for dispensing the mixture 152 onto or into one or more high-aspect ratio trench structures, as discussed herein.

By way of providing a real-world preparation example illustrating these steps, in one study the nano-particles comprised tungsten powder of 99.95% purity where the diameter of the tungsten particles is less than 1 µm, such as a tungsten powder. A suitable epoxy resin was employed as the carrier fluid. In this study tungsten powder having the above characteristics was mixed with epoxy resin and a cross-linker to facilitate setting. The resulting mixture was then loaded into a syringe for dispensing, though on a larger scale other suitable application devices may instead be employed.

Turning to the application aspects of the present technique, the loaded application device is used to apply (step 160) the mixture 152 to a surface (e.g., a wafer) in which trench structures or other high-aspect ratio features are formed. In this example a plastic sheet of other deformable membrane or layer with which the mixture 152 will not react is applied (step 162) over the surface on which the mixture 152 is applied. In the depicted example process flow, a roller is applied (step 164) to the plastic sheet and the roller is rolled (step 166) over the surface having trenches or grooves with a corresponding application of vertical force (i.e., downward or toward the surface) to force the mixture 152 into the trenches within the wafer or other structure. As discussed herein, other approaches for applying the mixture 152 within the trenches, such as screen-printing techniques, vacuum fill, injection (ink-jet)-compaction or use of a squeegee, may alternatively be employed.

In the present example process flow, after the mixture 152 is rolled into the grooves or trenches formed in the wafer or other structure, the deformable layer (e.g., plastic sheet) is removed (step 170) and any excess mixture 152 (e.g., mixture that is not within a trench or groove is removed (step 172) from the surface of the wafer, such as by scraping with a sharp or hard edge. The resulting structure has metallized trench structures 180 filled with high-Z nano-particles within the set or hardened mixture deposited within the trenches. Such metallized trench structures 180 may be part of a grating (e.g., a phase or absorption grating) of an imaging system or as part of some other MEMS device.

Figure 8:
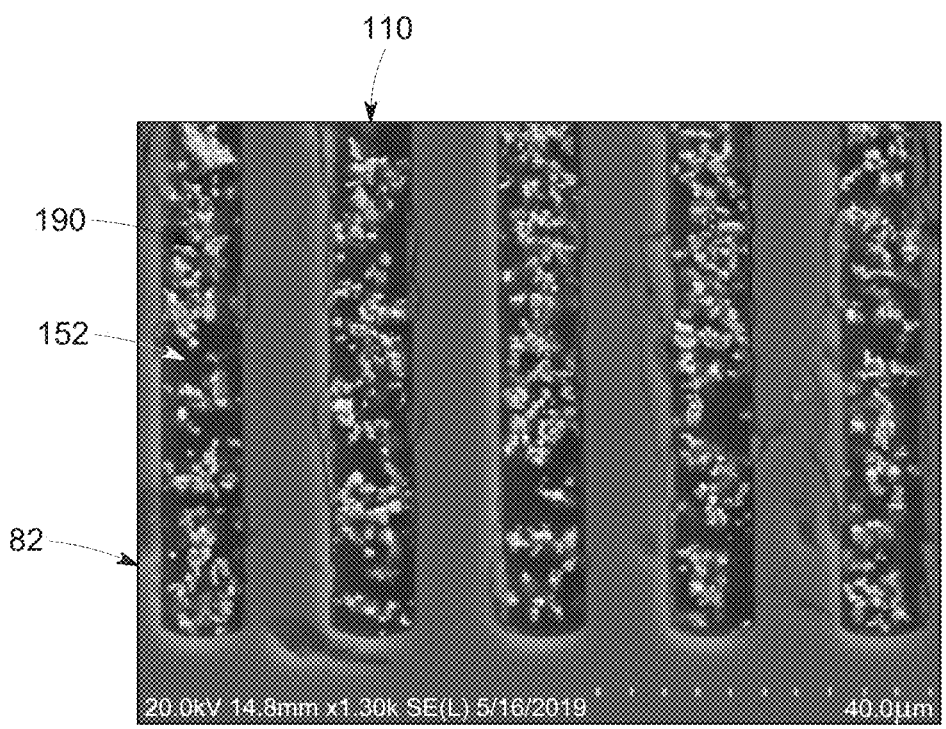
FIG. 8 depicts an additional cut-away view of nano-particle filled trenches, in accordance with certain aspects of the present disclosure.
Figure 9:
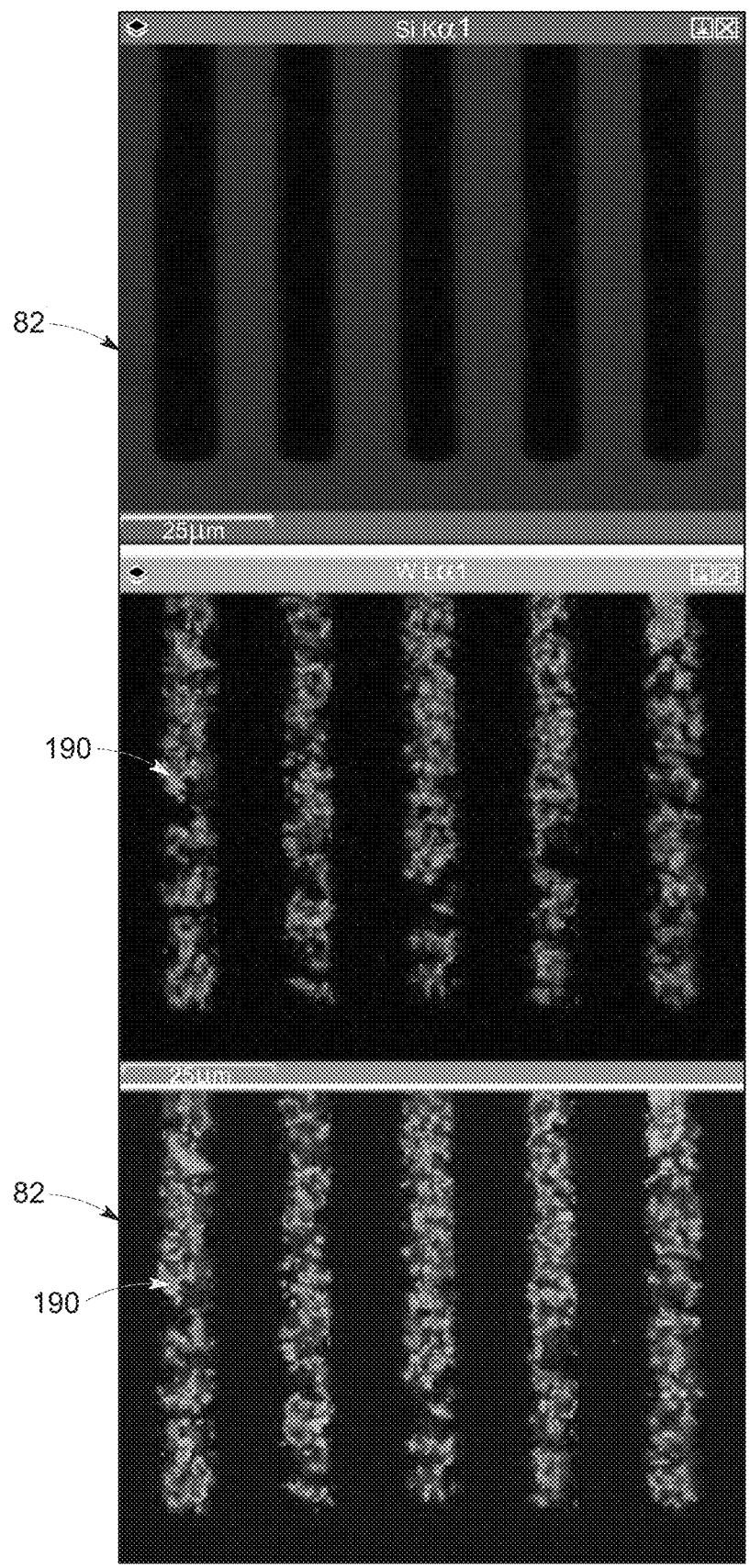
FIG. 9 depicts a cut-away element view of nano-particle filled trenches, in accordance with certain aspects of the present disclosure.

With the preceding in mind, an experimental study was performed to metallize trench structures using a mixture high-Z nano-particles and epoxy resin. In this study, prototype gratings (with a period 20 µm, a duty cycle of 50%, and an aspect ratio >20:1) were filled with tungsten nano-particles suspended in epoxy resin matrices through processes involving squeegeeing and rolling. These filled gratings were characterized through optical microscopy, secondary electron microscopy (SEM), both top-down and cross-sections imaging; energy dispersive X-ray spectroscopy of the SEM micrographs, and X-ray microscopy. Accompanying FIGS. 7-9 are cross-sectional images of metallized trench structures formed in accordance with these processes.

Figure 7:
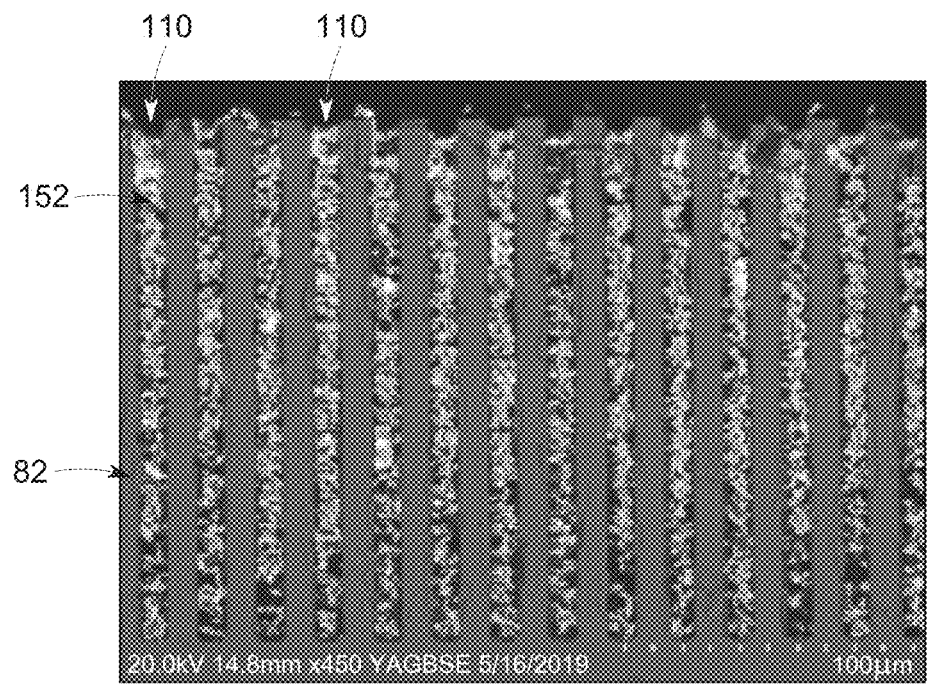
FIG. 7 depicts a cut-away view of nano-particle filled trenches, in accordance with certain aspects of the present disclosure.

For example, turning to FIG. 7 a high-aspect ratio trench structure is illustrated in a cut-away image generated using backscattered electrons (BSE) in scanning electron microscopy (SEM). In this example, the structure is formed from a silicon wafer 82 and 10 µm wide trenches 110 were roll-filled with a mixture 152 comprising tungsten nano-particles and epoxy resin. A close-up view of this structure is provided in FIG. 8, where discrete tungsten nano-particles 190 can be more readily discerned, suspended within the set epoxy that fills the trenches 110. FIG. 9 provides a series of elemental map images of this close up image in the form of a silicon image (uppermost), a tungsten image (middle), and a combined or composite image (bottom). As can be seen, the tungsten nano-particles effectively metallize the trenches in a substantially homogeneous and uniform manner.

Figure 10:
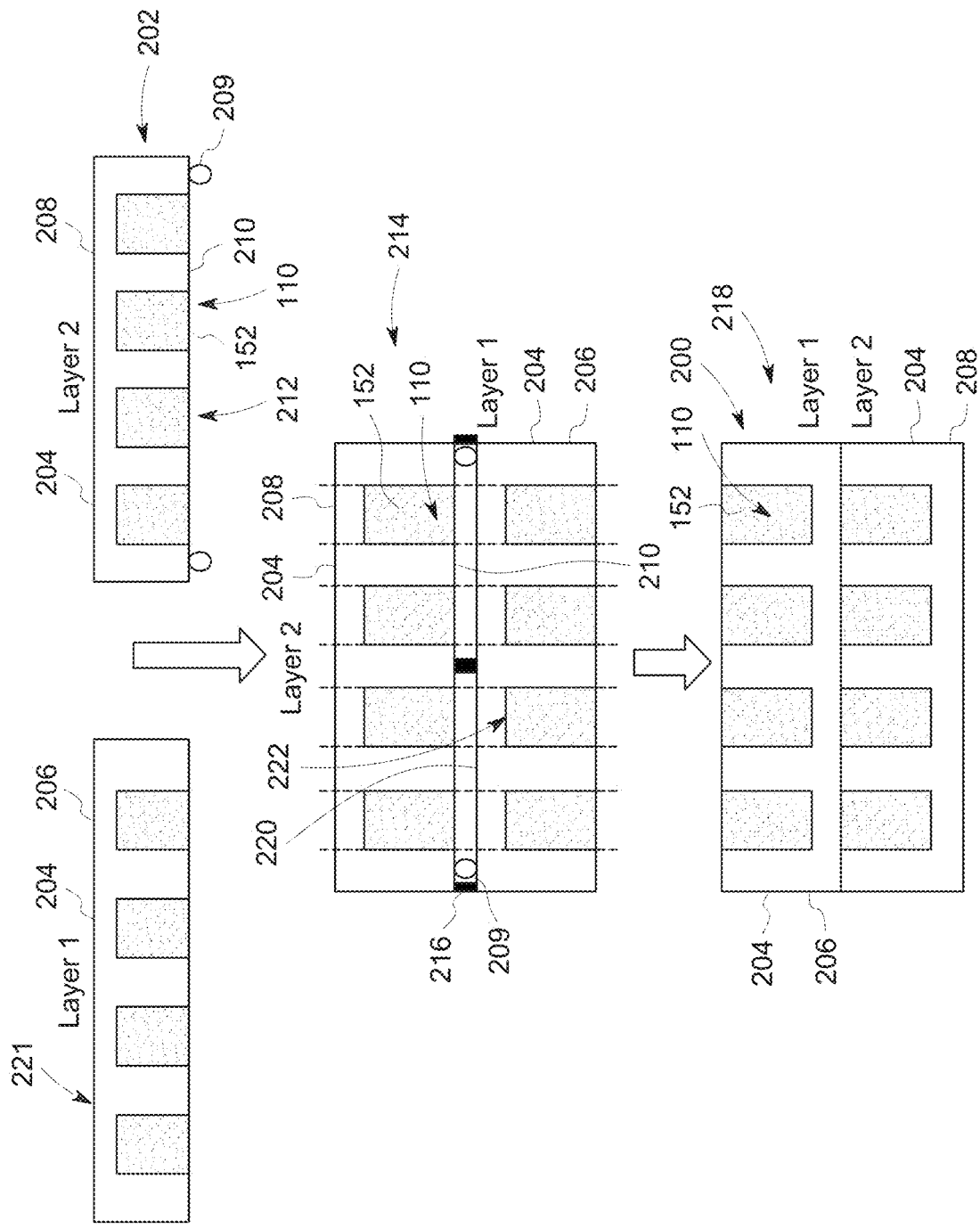
FIG. 10 depicts a flow diagram of steps of a process for forming a multi-layer stacked and bonded metallized structure or grating, in accordance with certain aspects of the present disclosure.

FIG. 10 depicts a flow diagram of steps of a process for forming a multi-layer stacked and bonded metallized structure or grating 200. In step 202 of the process, individual grating wafers or layers or grid structures 204 (e.g., layer 206 (layer 1) and layer 208 (layer 2)) are obtained following their individual fabrication utilizing the techniques described above. Although only two layers 204 are depicted in FIG. 10, more than two layers 204 (e.g., 3, 4, 5, or more layers 200) may be bonded together. Also, in step 202, a bonding agent 209 is applied to a surface 210 (e.g., adjacent a top 212 of the trenches 110 filled with nano-metallic powder containing composition 152). If three layers 204 were being bonded together, two of the layers 204 may have the bonding agent applied to the respective surface 210.

In step 214, the layers 204 are aligned (e.g., optically aligned) with respect to each other utilizing an optical camera of a wafer bonding system. Alignment is indicated by the dashed lines. During alignment of the layers 204, one or more spacers 216 are disposed between and kept engaged with the layers 206, 208. The spacers 216 are kept engaged with the layers 206, 208 via wedge error correction. The layers 204 are aligned so that trenches 210 in the same relative positions of the layers 204 are aligned and the trenches 210 are oriented in the same direction (e.g., upward or downward). In step 218, upon alignment of the layers 204, the one or more spacers 216 are removed and the layers 204 are brought in contact with each other. In particular, the surface 210 of the layer 208 is brought into contact with surface 220 (e.g., adjacent a bottom 221 of the trenches 110 filled with nano-metallic powder containing composition 152) of the layer 206. Upon contact between the layers 206, 208, the edges of the layers 206, 208 are clamped until the bonding agent is set. The bonded layers 206, 208 form the multi-layer stacked and bonded metallized structure or grating 200.

In the multi-layer stacked and bonded metallized structure or grating 200, due to the effective transparency of the silicon layer to X-rays along with the effective blocking of X-rays with the filled high Z-metal, the resulting structure effectively has higher aspect ratio metallized trenches 110 at defined periods for an imaging application, despite structurally having a break or intervening layer of silicon disposed between the trenches 110. Aligning and stacking multiple layers 204 in the stacked metallized structure 200 effectively increases the effective aspect ratio relative to a single layer by a multiple of the number of layers in the stacked metallized structure. For example, stacked metallized structures having 2, 3, 4, or more layers would have an effective aspect ratio of 2x, 3x, 4x, or more the aspect ratio of a single layer. In addition, the stack metallized structure is scalable with no upper limit on height. Further, the amount of metal per layer 204 may be increased due to the multiple layers 204 within the stacked metallized structure 200, thus, improving the ability to block/attenuate X-ray incident energies relative to a single layer. As a result, the signal-to-noise ratio as resolved by an imaging detector in an overall X-ray imaging system is improved.

Figure 11:
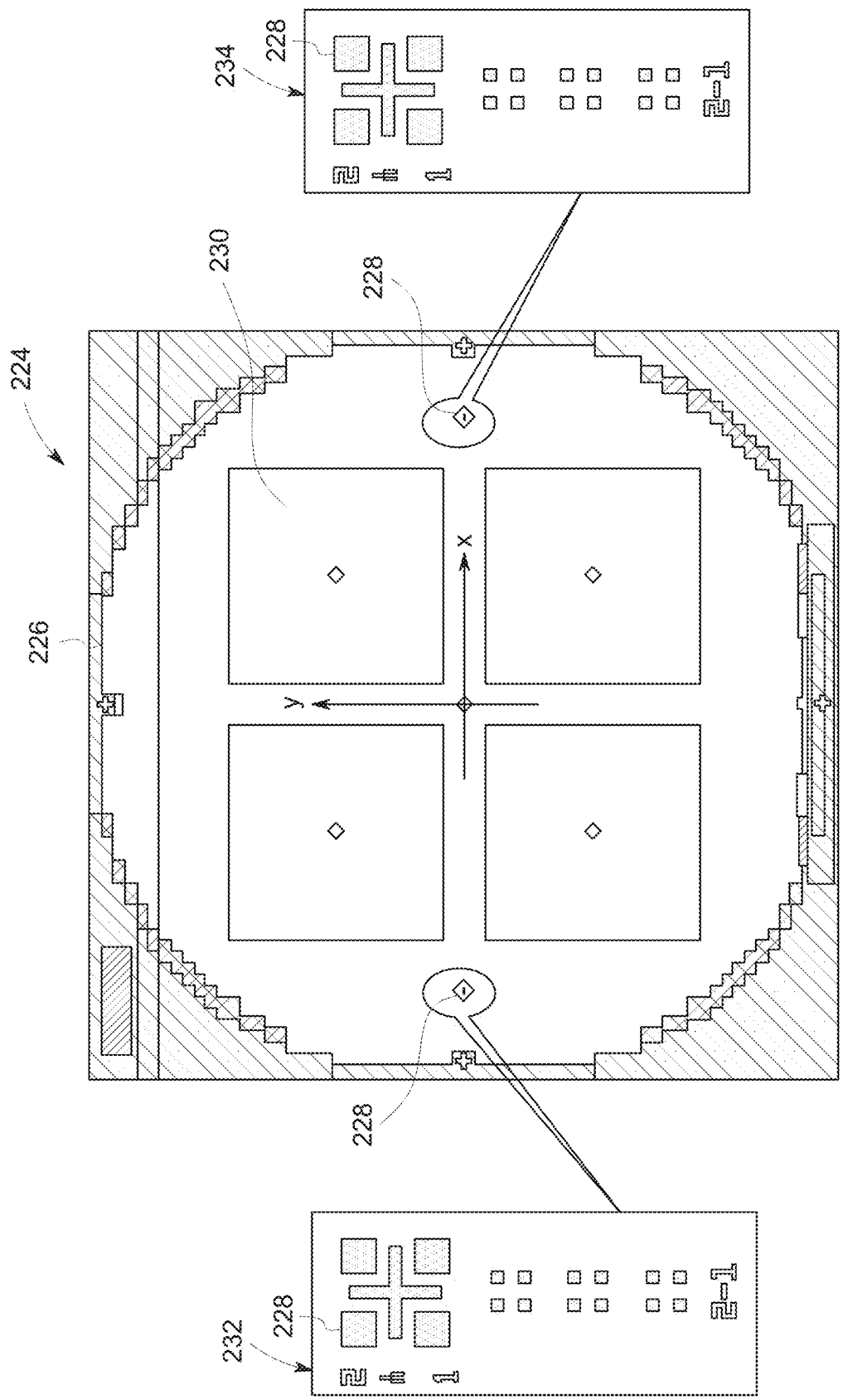
FIG. 11 depicts a schematic of a view, through an optical camera of a wafer bonding system, of a substrate having fiducial marks for aligning multiple layers to form a multi-layer stacked and bonded metallized structure or grating and associated zoomed in portions of the fiducial marks, in accordance with certain aspects of the present disclosure.

During alignment, the multiple layers (e.g., layers 204 in FIG. 10) are bonded together to form the stacked metallized structure (e.g., stacked metallized structure 200 in FIG. 10) on a substrate (e.g., silicon wafer). FIG. 11 depicts a schematic of a view 224, through an optical camera of a wafer bonding system, of a substrate 226 (e.g., silicon wafer) having fiducial marks 228 for aligning multiple layers to form a multi-layer stacked and bonded metallized structure or grating and associated zoomed in portions of the fiducial marks 228. The substrate 226 includes areas 230 for forming the multi-layer stacked and bonded metallized structure or grating. A first set 230 of fiducial marks 228 and a second set 232 of fiducial marks 228 flank the areas 230. The fiducial marks 228 are utilized to match features (e.g., trenches) of each grating layer with cross-hairs in the optical camera of the wafer bonding system in order to align the grating layers to form the multi-layer stacked and bonded metallized structure or grating.

Figure 12:
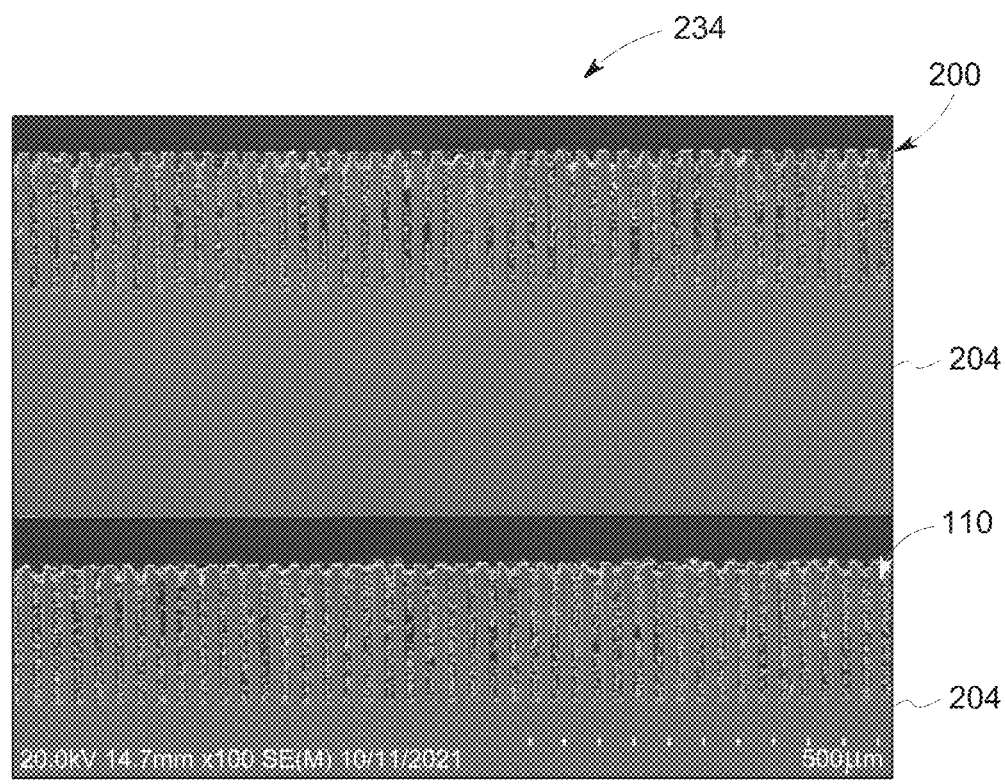
FIG. 12 depicts an image (e.g., secondary electron image) of a multi-layer stacked and bonded metallized structure or grating, in accordance with aspects of the present disclosure.
Figure 13:
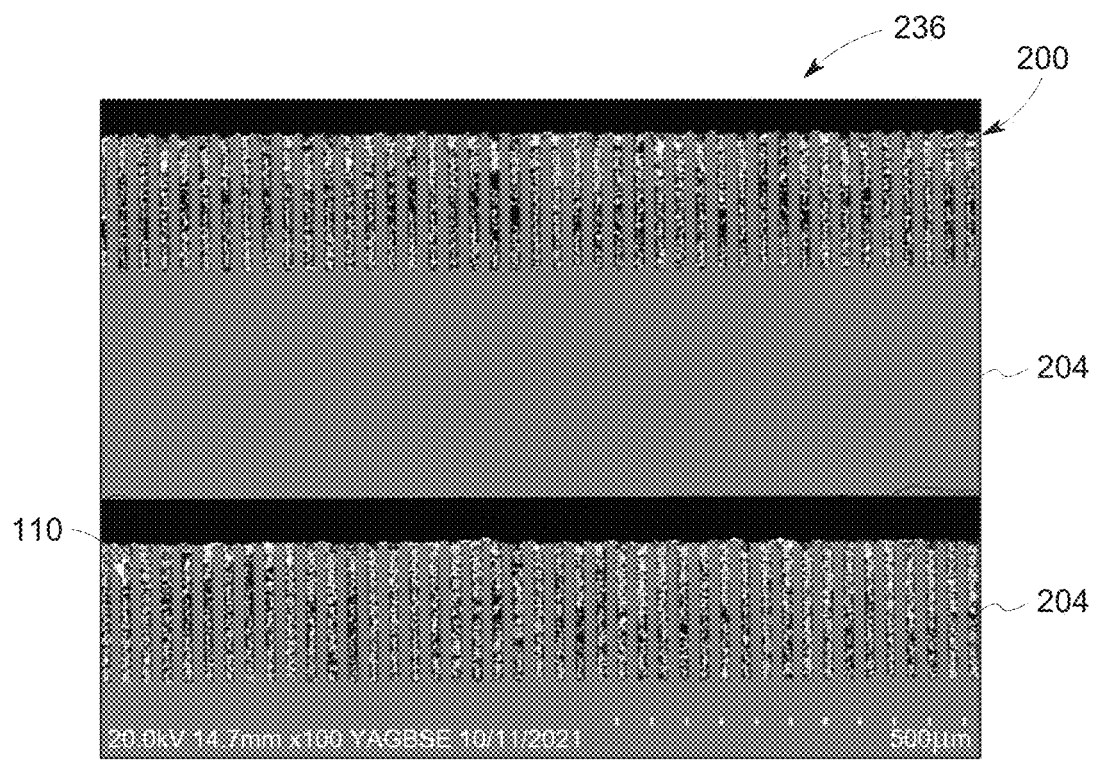
FIG. 13 depicts an image (e.g., backscattered electron image) of the multi-layer stacked and bonded metallized structure or grating in FIG. 12, in accordance with aspects of the present disclosure.

FIGS. 12 and 13 depict scanning electron micrograph images 234, 236 of the multi-layer stacked and bonded metallized structure or grating 200 (e.g., from the upper right area 230 in FIG. 11). The images 234, 236 depict the stacked layers 204 forming the multi-layer stacked and bonded metallized structure or grating 200. The images 234, 236 also depict the trench structures 110 filled with the nano-metallic powder containing composition 152 (e.g., high Z metal particulates dispersed within a resin matrix) for each layer 204. In particular, the composition 152 includes tungsten nano-particles suspended epoxy resin.

Figure 14:
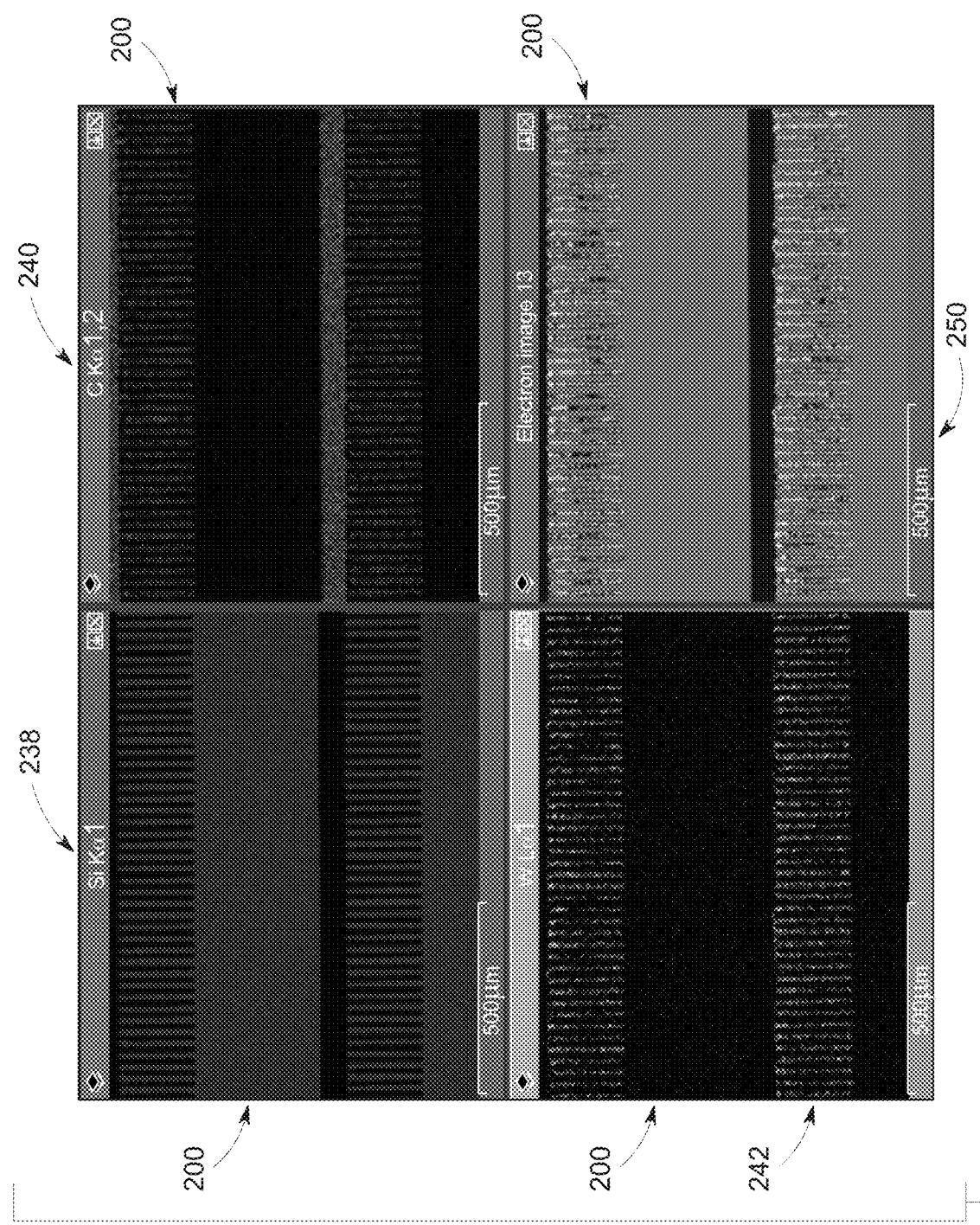
FIG. 14 depicts images of energy dispersive spectroscopy (EDS) maps (e.g., elemental maps) of the multi-layer stacked and bonded metallized structure or grating in FIG. 12, in accordance with aspects of the present disclosure.
Figure 15:
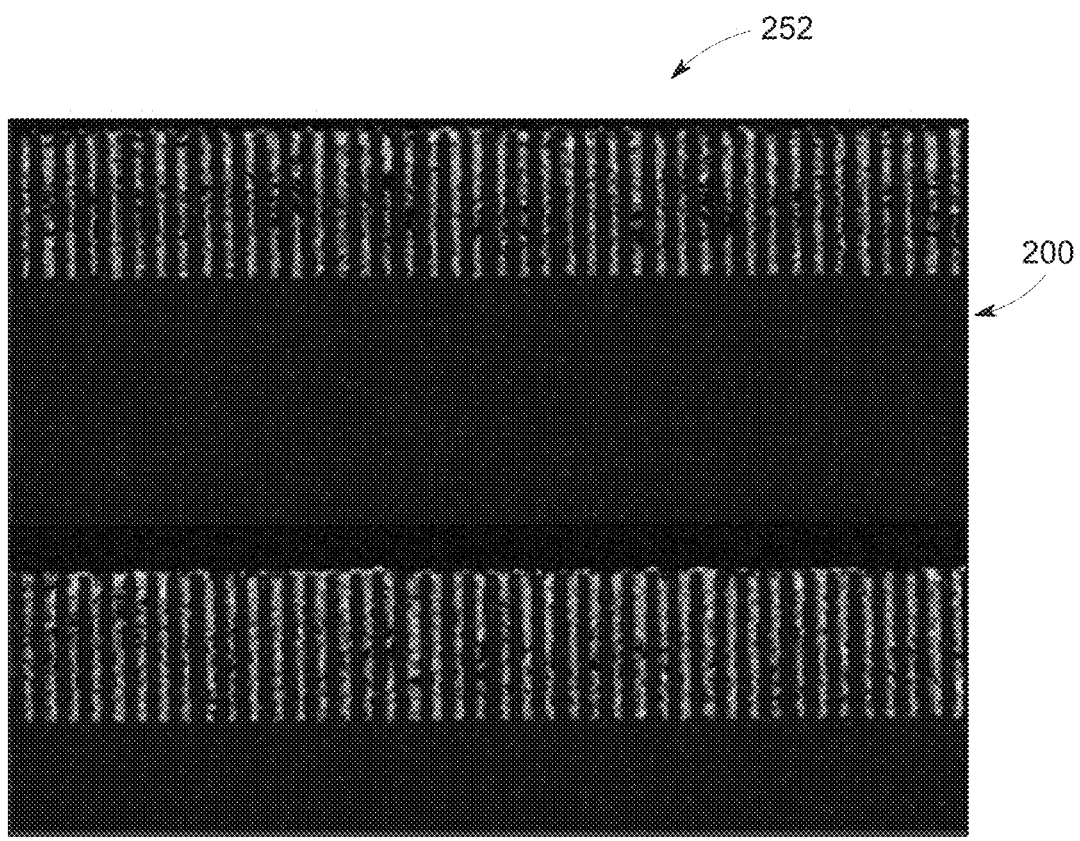
FIG. 15 depicts an image of an overlay of silicon and tungsten maps of the EDS maps in FIG. 14, in accordance with aspects of the present disclosure.

FIG. 14 depicts images 238, 240, 242, and 244 of EDS maps (e.g., elemental maps) of the multi-layer stacked and bonded metallized structure or grating 200 in FIG. 12. Image 238 represents a silicon elemental map. Image 240 represents a carbon elemental map. Image 242 represents a tungsten elemental map. Image 244 represents a scanning electron micrograph image of the multi-layer stacked and bonded metallized structure or grating 200 from which the EDS maps are derived. FIG. 15 depicts an image 252 (e.g., composite image) of an overlay of the silicon and tungsten maps (i.e., images 238 and 242) of the EDS maps in FIG. 14. As depicted in FIG. 15, the tungsten nano-particles effectively metallize the trenches in a substantially homogeneous and uniform manner.

Figure 16:
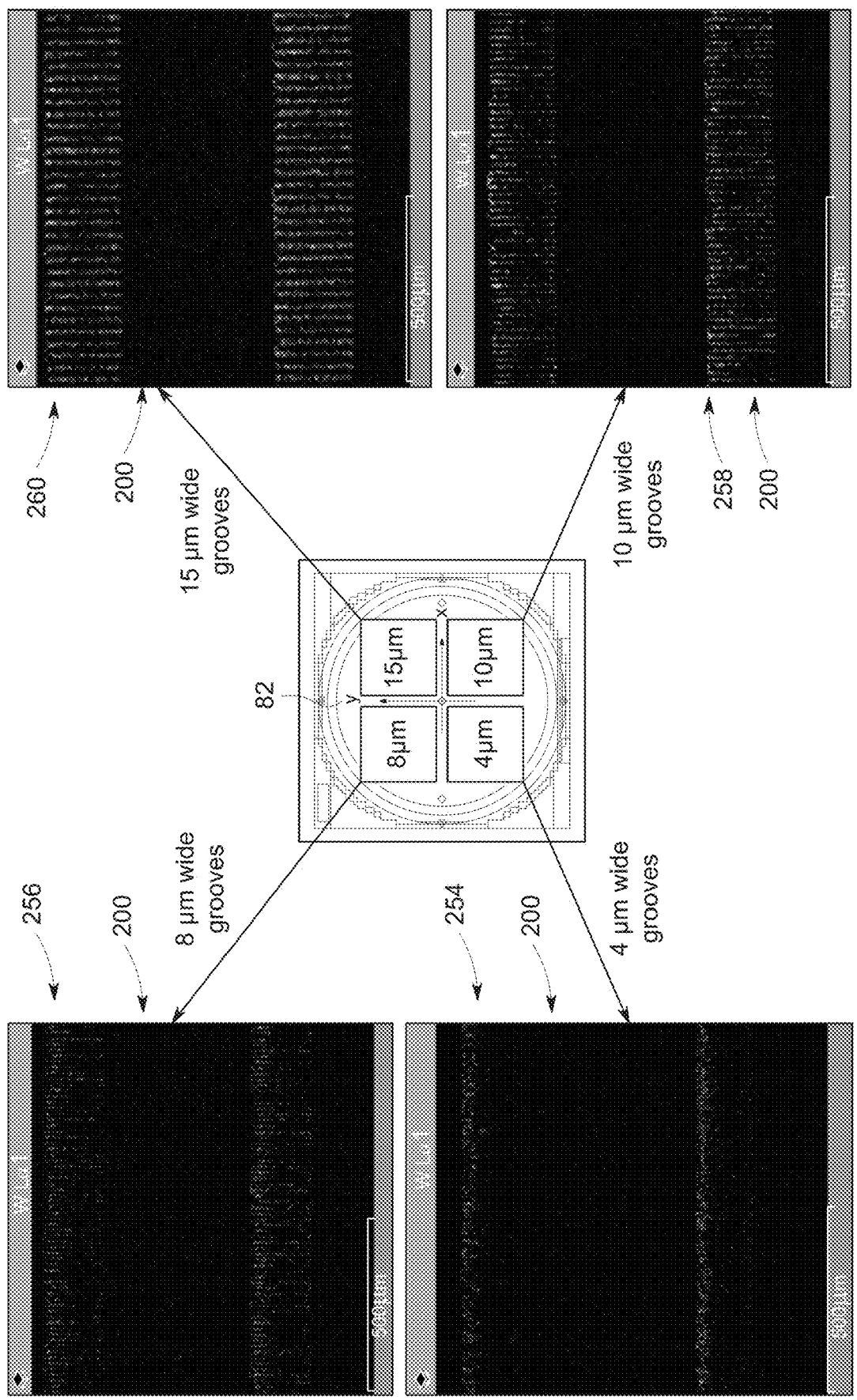
FIG. 16 illustrates using a schematic and images, examples of high-aspect ratio trenches formed in accordance with certain aspects of the present disclosure.

Aspects of these studies are illustrated in FIG. 16 where a representation of a silicon wafer 82, processed as described above, is schematically illustrated along with EDS maps (e.g., elements maps) illustrating the trench structure formed in different multi-layer stacked and bonded metallized structures or gratings 200 using the techniques described herein. Images 254, 256, 258, and 260 represent tungsten maps of the different multi-layer stacked and bonded metallized structures or gratings 200. The multi-layer stacked and bonded metallized structure 200 in image 254 includes a trench structure, where each groove or trench has a width of 4 micrometers (e.g., µm). The multi-layer stacked and bonded metallized structure 200 in image 256 includes a trench structure, where each groove or trench has a width of 8 μm. The multi-layer stacked and bonded metallized structure 200 in image 258 includes a trench structure, where each groove or trench has a width of 10 μm. The multi-layer stacked and bonded metallized structure 200 in image 260 includes a trench structure, where each groove or trench has a width of 15 μm. As depicted in the images 254, 256, 258, and 260, the tungsten nano-particles effectively metallize the trenches in a substantially homogeneous and uniform manner. As the grooves increase in width, the tungsten fill or amount of overall tungsten disposed within the grooves increases for the multi-layer stacked and bonded metallized structures 200. In certain embodiments, the grooves may have a minimum 0.5 μm and still be effectively metallized.

Figure 17:
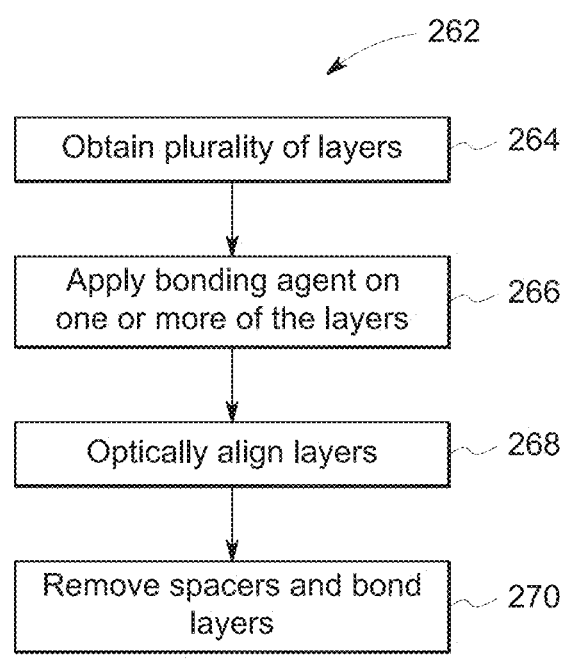
FIG. 17 illustrates a flow chart of a process for forming a multi-layer stacked and bonded metallized structure or grating, in accordance with certain aspects of the present disclosure.

FIG. 17 illustrates a flow chart of a process 262 for forming a multi-layer stacked and bonded metallized structure or grating. The process 262 includes obtaining a plurality of individual grating wafers or layers or grid structures (step 264). The obtained layers were already individually fabricated (i.e., having metallized trenches) utilizing the techniques described above. The number of layers bonded together to fabricate the multi-layer stacked and bonded metallized structure or grating may be 2, 3, 4, 5 or more layers. The process 262 also includes applying bonding agent to a respective surface (e.g., adjacent a top of the trenches filled with nano-metallic powder containing composition) of one or more of the plurality of layers (step 266). For example, if two layers are being bonded together, then one layer may have the bonding agent applied to a surface. If three layers are being bonded together, two of the layers may have the bonding agent applied to the respective surfaces.

The process 262 further includes optically aligning the plurality of layers with respect to each other utilizing an optical camera of a wafer bonding system (step 268). During alignment of the plurality of layers, one or more spacers are disposed between and kept engaged between adjacent layers. The spacers are kept engaged with the layers via wedge error correction. The layers are aligned so that trenches in the same relative positions of the layers are aligned and the trenches are oriented in the same direction (e.g., upward or downward). The optical alignment may occur utilizing fiducial marks on a substrate (e.g., silicon wafer) that flank an area that the plurality of layers are being bonded together in to form the multi-layer stacked and bonded metallized structure or grating. The process 262 further includes, upon alignment of the layers, removing the one or more spacers and bonding the layers together by bringing the layers in contact with each other (step 270). In particular, the respective surface(s) of the layer(s) are brought into contact with respective surface(s) (e.g., adjacent a bottom of the trenches filled with nano-metallic powder containing composition) of adjacent layer(s). Upon contact between the layers, the edges of the layers are clamped until the bonding agent is set. The bonded layers form the multi-layer stacked and bonded metallized structure or grating.

Technical effects of the disclosed embodiments include the fabrication of high-aspect ratio (i.e., greater than 20:1) metallized structures for various devices (e.g., X-ray imaging gratings and other trenched and/or segmented gratings, capacitive MEMS, electrostatic MEMS, inertial MEMS, other MEMS structures, Through Silicon Vias (TSVs), Fin-FETs, Interconnect structures in SOC/CMOS, etc.). Each metallized structure include multiple layers in an aligned and stacked arrangement. Aligning and stacking multiple effectively increases the effective aspect ratio in trench structures in the stacked metallized structure. In addition, the stack metallized structure is scalable with no upper limit on height. Further, the amount of metal per layer may be increased due to the multiple layers within the stacked metallized structure, thus, improving the ability to block/attenuate X-ray incident energies relative to a single layer. As a result, the signal-to-noise ratio as resolved by an imaging detector in an overall X-ray imaging system is improved.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for forming a multi-layered, stacked grid structure, comprising:
   aligning a first grid structure with a second grid structure, wherein both the first grid structure and the second grid structure each comprise a substrate in which a plurality of trenches are formed and a cured carrier fluid disposed within the plurality of trenches, and wherein a plurality of nano-particles are suspended within the cured carrier fluid; and
   upon aligning the first grid structure and the second grid structure so that their respective plurality of trenches are aligned in the same orientation, joining the first grid structure and the second grid structure together to form the multi-layered, stacked grid structure.

2. The method of claim 1, comprising, prior to aligning the first grid structure with the second grid structure applying a bonding agent to a first surface of the first grid structure.

3. The method of claim 2, wherein aligning the first grid structure with the second grid structure comprises keeping one or more spacers engaged between the first surface of the first grid structure and a second surface of the second grid structure through wedge error correction during alignment, wherein the second surface is configured to contact the first surface of the first grid structure upon joining the first grid structure and the second grid structure together.

4. The method of claim 3, wherein the second surface is adjacent a bottom of the plurality of trenches of the second grid structure, and the first surface is adjacent a top of the plurality of trenches of the first grid structure.

5. The method of claim 3, comprising, upon aligning the first grid structure with the second grid structure, removing the one or more spacers, and wherein joining the first grid structure and the second grid structure together comprises bringing the first grid structure and the second grid structure in contact upon removal of the one or more spacers and clamping the first grid structure and the second grid structure at the edges until the bonding agent is set.

6. The method of claim 1, wherein aligning the first grid structure with the second grid structure comprises utilizing fiducial marks disposed on an additional substrate separate from respective substrates of first grid structure and the second grid structure in conjunction with an optical camera of a wafer bonding system.

7. The method of claim 1, wherein the plurality of nano-particles comprise a high-Z material.

8. The method of claim 1, wherein the plurality of nano-particles comprise at least one of hafnium, tantalum, tungsten, rhenium, osmium, iridium, platinum, gold, mercury, thallium, lead, bismuth, polonium, or depleted uranium.

9. The method of claim 1, wherein the multi-layered, stacked grid structure is a component of an imaging grating, a capacitive MEMS device, an electrostatic MEMS device, a magnetic MEMS device, an electromagnetic MEMS device, a radiofrequency MEMS device, or an inertial MEMS device.

10. The method of claim 1, wherein the cured carrier fluid comprises an epoxy resin matrix.

11. A method for forming a stacked metallized grid structure, comprising:
   optically aligning a plurality of metallized grid structures on a substrate utilizing an optical camera of a wafer bonding system and fiducial marks on the substrate, wherein each metallized grid structure of the plurality of metallized grid structures comprises a respective substrate in which a plurality of trenches are formed and a cured carrier fluid disposed within the plurality of trenches, wherein a plurality of nano-particles having a high Z material are suspended within the cured carrier fluid; and
   upon optically aligning the plurality of metallized grid structures so that their respective plurality of trenches are aligned in the same orientation, joining the plurality of metallized grid structures together to form the stacked metallized grid structure.

12. The method of claim 11, wherein the plurality of metallized grid structures comprises a first metallized grid structure and a second metallized grid structure, prior to aligning the first grid metallized grid structure with the second metallized grid structure applying a bonding agent to a first surface of the first metallized grid structure.

13. The method of claim 12, wherein aligning the first metallized grid structure with the second metallized grid structure comprises keeping one or more spacers engaged between the first surface of the first metallized grid structure and a second surface of the second metallized grid structure through wedge error correction during alignment, wherein the second surface is configured to contact the first surface of the first grid structure upon joining the first metallized grid structure and the second metallized grid structure together.

14. The method of claim 13, wherein the second surface is adjacent a bottom of the plurality of trenches of the second metallized grid structure, and the first surface is adjacent a top of the plurality of trenches of the first metallized grid structure.

15. The method of claim 13, comprising, upon aligning the first metallized grid structure with the second metallized grid structure, removing the one or more spacers, and wherein joining the first metallized grid structure and the second metallized grid structure together comprises bringing the first metallized grid structure and the second metallized grid structure in contact upon removal of the one or more spacers and clamping the first metalized grid structure and the second metallized grid structure at the edges until the bonding agent is set.

16. The method of claim 11, wherein the plurality of nano-particles comprise at least one of hafnium, tantalum, tungsten, rhenium, osmium, iridium, platinum, gold, mercury, thallium, lead, bismuth, polonium, or depleted uranium.

17. The method of claim 11, wherein the multi-layered, stacked grid structure is a component of an imaging grating, a capacitive MEMS device, an electrostatic MEMS device, a magnetic MEMS device, an electromagnetic MEMS device, a radiofrequency MEMS device, or an inertial MEMS device.

18. The method of claim 11, wherein the cured carrier fluid comprises an epoxy resin matrix.

19. An imaging grating, comprising:
   a plurality of metallized grid structures bonded together in a stacked arrangement, wherein each metallized grid structure of the plurality of metallized grid structures comprises a respective substrate in which a plurality of trenches are formed and a cured carrier fluid disposed within the plurality of trenches, wherein a plurality of nano-particles having a high Z material are suspended within the cured carrier fluid, wherein the respective plurality of trenches of the plurality of metallized grid structures are aligned in the same orientation, and wherein each metallized grid structure was individually fabricated prior to bonding of the plurality of metallized grid structures together.

20. The imaging grating of claim 19, wherein the plurality of nano-particles comprises tungsten.

* * * * *